United States Patent

Torimitsu et al.

[11] Patent Number: 5,965,320
[45] Date of Patent: Oct. 12, 1999

[54] POSITIVE PHOTORESIST COMPOSITION CONTAINING PHENOL ESTER OF 1,2-NAPTHOQUINONE-(2)-DIAZIDE-6-SULFONIC ACID AND PATTERN FORMATION METHOD USING THE COMPOSITION

[75] Inventors: Kazue Torimitsu; Yuko Urano; Hideo Kikuchi, all of Funabashi, Japan

[73] Assignee: Toyo Gosei Kogyo Co., Ltd., Japan

[21] Appl. No.: 08/117,546

[22] Filed: Sep. 7, 1993

Related U.S. Application Data

[63] Continuation of application No. 07/777,572, Oct. 16, 1991, abandoned.

[30] Foreign Application Priority Data

Oct. 18, 1990 [JP] Japan ..................................... 2-277876
Dec. 27, 1990 [JP] Japan ..................................... 2-415297

[51] Int. Cl.⁶ .................................................... G03F 7/023
[52] U.S. Cl. ........................ 430/192; 430/193; 430/325; 430/326; 430/945
[58] Field of Search .................................. 430/191, 192, 430/193, 325, 326, 945

[56] References Cited

U.S. PATENT DOCUMENTS

| | | | |
|---|---|---|---|
| 3,046,112 | 7/1962 | Schmidt et al. | 534/557 |
| 3,130,047 | 4/1964 | Uhlig et al. | 430/193 |
| 3,130,048 | 4/1964 | Fritz et al. | 430/193 |
| 3,184,310 | 5/1965 | Fritz et al. | 430/193 |
| 3,188,210 | 6/1965 | Fritz et al. | 430/193 |
| 3,269,837 | 8/1966 | Süs | 430/193 |
| 4,812,880 | 3/1989 | Ogawa et al. | 430/193 |
| 5,084,372 | 1/1992 | Hsieh et al. | 430/945 |
| 5,110,706 | 5/1992 | Yumoto et al. | 430/193 |
| 5,215,857 | 6/1993 | Hosaka et al. | 430/191 |

Primary Examiner—Christopher G. Young
Attorney, Agent, or Firm—Bierman, Muserlian and Lucas

[57] ABSTRACT

A positive photoresist composition including an alkali-soluble resin and a photosensitive agent including 1,2-naphthoquinone-diazide group.

A first composition wherein the photosensitive agent is an ester of 1,2-naphthoquinone-(2)-diazide-6-sulfonic acid and alcohols or phenols, or a sulfonamide of 1,2-naphthoquinone-(2)-diazide-6-sulfonic acid and organic amines.

A second composition wherein the photosensitive agent comprises (a) an ester compound of 1,2-naphthoquinone-(2)-diazide-6-sulfonic acid and phenols and (b) an ester of 1,2-naphthoquinone-(2)-diazide-5-sulfonic acid and phenols and/or an ester of 1,2-naphthoquinone-(2)-diazide-4-sulfonic acid and phenols.

A third composition wherein the photosensitive agent is a product obtained by condensation of phenols with (a) 1,2-naphthoquinone-(2)-diazide-6-sulfonylhalide and (b) 1,2-naphthoquinone-(2)-diazide-5-sulfonylhalide and/or 1,2-naphthoquinone-(2)-diazide-4-sulfonylhalide.

A pattern formation method using the above positive photoresist compositions including:

(1) forming a positive photoresist layer on a substrate,
(2) exposing the positive photoresist layer to a predetermined pattern, and
(3) developing the positive photoresist layer with an alkaline developing solution.

This invention allows flexible setting of parameters A and B of the photoresist over a fairly wide range and is particularly suitable for use in the formation of fine patterns for various semiconductor ICs and magnetic valves.

12 Claims, No Drawings

POSITIVE PHOTORESIST COMPOSITION CONTAINING PHENOL ESTER OF 1,2-NAPTHOQUINONE-(2)-DIAZIDE-6-SULFONIC ACID AND PATTERN FORMATION METHOD USING THE COMPOSITION

This application is a continuation of application Ser. No. 07/77572 filed Oct. 16, 1991, now abandoned.

FIELD OF THE INVENTION

This invention relates to a novel positive photoresist composition sensitive to radiation, more specifically to a positive photoresist composition suitable for exposure to radiation of a specific wavelength, and a pattern formation method using this composition.

BACKGROUND OF THE INVENTION

A positive photoresist generally uses an alkali-soluble resin, mixed with a naphthoquinonediazide compound as a dissolution inhibitor. The alkali-soluble resin is generally novolac resin. A positive photoresist using the novolac resin is useful because it can be developed with an alkaline aqueous solution without swelling, which provides very good resolution, and especially because it has a high resistance to plasma etching when the resulting image is used as an etching mask. With increasing integration and fine patterns due to recent advance in semiconductor technology, photoresists are required to have resolutions of one-half micron or better.

Currently, in the formation of fine patterns used in various semiconductor integrated circuits and magnetic valves, the photoresist is exposed mainly by reduced projection exposure. The resolution R in reduced projection exposure follows Rayleigh's Equation (1):

$$R = k \frac{\lambda}{NA} \quad (1)$$

There are three methods to improve this resolution: (1) numerical aperture NA of the lens is increased, (2) wavelength ($\lambda$) of exposure light is decreased, and (3) constant k, which is determined by the resist process, is reduced.

Heretofore, improvement of resolution has been predominantly achieved by increasing the NA of the stepper and improving the resist process. However, increasing NA of the lens also decreases the depth of focus (DOF), in accordance with Equation (2):

$$DOF = \pm \frac{\lambda}{2(NA)^2} \quad (2)$$

On the other hand, since decreasing the wavelength $\lambda$ has much smaller influence on DOF than increasing NA, reduced projection exposure devices which use the shorter wavelength i-line (365 nm wavelength) of a mercury lamp, rather than the g-line (436 nm wavelength) of a mercury lamp in the prior art systems, along with photoresists for use with these devices have recently been developed. Currently, commercial i-line photoresists use predominantly phenol esters of 1,2-naphthoquinonediazide-4-sulfonic acid or 1,2-naphthoquinonediazide-5-sulfonic acid as dissolution inhibitors, which are the same as those used for g-line photoresists. However, the above i-line photoresists provide insufficient resolution, and the resulting resist patterns are not satisfactory.

This is because, when used for i-line radiation (compared with the use for g-line radiation), the dissolution inhibitor, the above-mentioned phenol esters are low in transmissivity, so that it is difficult for light to reach the bottom of the photoresist, resulting in large differences in the amounts of exposure between the top and bottom of the photoresist.

Therefore, if the content of the dissolution inhibitor is reduced to increase the transmissivity of the photoresist to i-line radiation, the difference in solubility of the developing solution between the exposed portion and unexposed portion of the photoresist tends to become small, resulting in film loss.

Another problem of prior art positive photoresists is a low sensitivity to long-wavelength light such as that generated by an argon laser or the like. For example, in the fabrication of an optical disk base plate, in which a positive photoresist coated on a glass disk is exposed to an argon ion laser to form bits, the exposure requires a long time because the prior art photoresist has almost no absorption at the 488 nm wavelength generated by the argon ion laser.

Recently, the details of the photoreaction mechanism of naphthoquinonediazide-based photosensitive agents have been well elucidated, and the correlation between the photosensitivity characteristics of photoresist and its performance has been clarified (e.g. "Ultra-Fine Processing and Resist Materials" 1985, published by CMC K. K.). Parameters indicative of the photosensitivity characteristics include photoreaction parameters A and B, which are values related to the ratio of T (transmissivity), proposed by Dill et al. (Dill et al., IEEE, Trans. B. D., Vol.22, No.7, p.445).

As shown in the following Equations (3) and (4), A represents the ratio of transmissivities before and after exposure, and B represents the transmissivity after exposure $$A = (1/d) l_n [T(\infty)] \quad (3)$$

$$B = -(1/d) l_n T(\infty) \quad (4)$$

wherein d is the film thickness of the photoresist, T(o) is the transmissivity of the photoresist before exposure, and T($\infty$) is the transmissivity of the photoresist after exposure.

It has been known that the resist performance is varied by varying parameters A and B which are indicative of the photosensitivity characteristics of photoresist. Therefore, to design a high-resolution photoresist, it is necessary to optimize parameters A and B according to the intended application.

However, for 1,2-naphthoquinone-(2)-diazide-5-sulfonic acid or 1,2-naphthoquinone-(2)-diazide-4-sulfonic acid and phenols alone, which are photosensitive agents used for prior art photoresists, the only way to vary the parameters A and B of the photoresist, especially the value of the former, at g-line (436 nm) or i-line (365 nm) is to vary the ratio of the amounts of photosensitive agents, that is, the ratio of the photosensitive agent to the alkali-soluble resin. However, increasing the amount of the photosensitive agent increases the value of parameter A, but decreases the sensitivity, and decreasing the amount of the photosensitive agent decreases the value of parameter A, but tends to cause a film loss.

SUMMARY OF THE INVENTION

With the view to eliminate the above prior art problems, it is a primary object of the present invention to provide a positive photoresist composition, which is high in transmissivity to i-line radiation, has a large difference in solubility in the developing solution between the exposed portion and unexposed portion, and uses a high-resolution positive photoresist composition which allows flexible designing of parameters A and B of the photoresist at i-line radiation, The invention also provides a pattern formation method using the positive photoresist composition.

Another object of the present invention is to provide a positive photoresist composition which is highly sensitive to light generated by an argon ion laser and a pattern formation method using said composition.

The inventors have conducted intensive studies to attain the above objects, and found that a positive photoresist composition can be obtained, which exhibits a very large difference in solubility in the developing solution between the exposed portion and the unexposed portion. Moreover, it has an absorption at a longer wavelength than prior art positive photoresists, providing high sensitivity to exposure to an argon ion laser. These advantages are achieved by using an alkali-soluble resin and a quinonediazide compound having a specific structure.

Based on the above findings, the present invention provides a positive photoresist composition comprising an alkali-soluble resin and a photosensitive agent including 1,2-naphthoquinonediazide group. The photosensitive agent is an ester of 1,2-naphthoquinone-(2)-diazide-6-sulfonic acid with alcohols or phenols, or a sulfonamide which is the reaction product of 1,2-naphthoquinone-(2)-diazide-6-sulfonic acid with organic amines. In a second positive photoresist composition according to the present invention, the photosensitive agent comprises (a) an ester of 1,2-naphthoquinone-(2)-diazide-6-sulfonic acid and phenols and (b) an ester of 1,2-naphthoquinone-(2)-diazide-5-sulfonic acid and phenols and/or an ester of 1,2-naphthoquinone-(2)-diazide74-sulfonic acid and phenols.

In a third inventive positive photoresist composition, the photosensitive agent is a product obtained by condensation of phenols with (a) 1,2-naphthoquinone-(2)-diazide-6-sulfonylhalide and (b) 1,2-naphthoquinone-(2)-diazide-5-sulfonylhalide and/or 1,2-naphthoquinone-(2)-diazide-4-sulfonylhalide.

There is also provided, according to the present invention, a pattern formation method using the inventive positive photoresist composition comprising:

(1) forming the inventive positive photoresist as a layer on a substrate, (2) exposing the layer to a predetermined pattern, and (3) developing the layer with an alkaline developing solution.

It is particularly preferable that, in the foregoing method, the positive photoresist layer is exposed to i-line radiation of a mercury lamp, or to argon ion laser radiation.

It has been found that the present invention can solve the prior art problems by using an ester or an amide of the quinonediazide as a dissolution inhibitor. This is because the inventive positive photoresist composition (1) is high in transmissivity of i-line radiation, (2) has an absorption at the longer wavelength side, and (3) is very high in dissolution inhibition ability.

It has also been found that the present invention can provide a positive photoresist composition which allows parameter A at the i-line to be varied over a relatively wide range and can optimize parameters A and B without a reduction in sensitivity or film loss.

Since the photosensitive agents used in the present invention, e.g. esters of 1,2-naphthoquinone-(2)-diazide-6-sulfonic acid and alcohols (hereinafter referred to as "6-alcohol esters"), esters of 1,2-naphthoquinone-(2)-diazide-6-sulfonic acid and phenols (hereinafter referred to as "6-phenol esters"), sulfonamides of 1,2-naphthoquinone-(2)-diazide-6-sulfonic acid and organic amines (hereinafter referred to as "6-sulfonamides"), esters of 1,2-naphthoquinone-(2)-diazide-5-sulfonic acid and phenols (hereinafter referred to as "5-phenol esters"), and esters of 1,2-naphthoquinone-(2)-diazide-4-sulfonic acid and phenols (hereinafter referred to as "4-phenol esters"), differ from each other in absorbance at both the g-line and i-line, T(o) in Equation (3) can be varied over a fairly wide range by combining these compounds.

The above object can also be attained using a product obtained by condensation of phenols with (a) 1,2-naphthoquinone-(2)-diazide-6-sulfonylhalide (hereinafter referred to as "NAH-6") and (b) 1,2-naphthoquinone-(2)-diazide-5-sulfonylhalide (hereinafter referred to as "NAH-5") and/or 1,2-naphthoquinone-(2)-diazide-4-sulfonylhalide (hereinafter referred to as "NAH-4").

DETAILED DESCRIPTION OF THE INVENTION

The alkali-soluble resin used in the present invention can be novolac resin, poly(hydroxystyrene) or its derivatives, a copolymer having repeated structures of Formula (I):

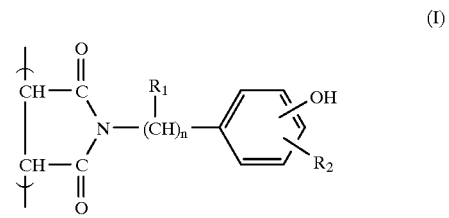

wherein $R_1$ is hydrogen, alkyl or aryl; R2 is hydrogen, halogen, alkyl or alkoxy; and n is an integer from 0 to 6.

The novolac resin is obtained by condensing phenols and ketones or aldehydes in the presence of an acid catalyst. Phenols used in the condensation include, for example, phenol, o-cresol, m-cresol, p-cresol, o-ethylphenol, m-ethylphenol, p-ethylphenol, o-butylphenol, m-butylphenol, p-butylphenol, 2,3-xylenol, 2,4-xylenol, 2,5-xylenol, 3,4-xylenol, 3,5-xylenol, p-phenylphenol, hydroquinone, catechol, resorcinol, pyrogallol, α-naphthol, β-naphthol, bisphenol A or the like. These phenols can be used alone or in combination.

The ketones or aldehydes include formaldehyde, paraformaldehyde, acetaldehyde, propionaldehyde, benzaldehyde, acetone, methylethylketone and the like. These compounds can be used alone or in combination.

The poly(hydroxystyrene) and its derivatives are obtained by polymerization of one or more hydroxystyrenes or copolymerization thereof with other acrylic monomers. The hydroxystyrenes include o-hydroxystyrene, m-hydroxystyrene, p-hydroxystyrene, 3-methyl-4-hydroxystyrene, 3,5-dimethyl-4-hydroxystyrene, α-methyl-o-hydroxystyrene, α-methyl-m-hydroxystyrene, and α-methyl-p-hydroxystyrene. The acrylic monomers as copolymerization ingredients include acrylic esters, methacrylic esters, acrylamide, methacrylamine, and acrylonitrile.

The copolymers represented by Formula (I) having repeated structures of maleimide derivative are disclosed, for example, in Japanese Patent Publication Laid-open (hereinafter OPI) 61-162033/1986, OPI 62-151408/1987, and OPI 62-151409/1987.

The quinonediazide compound used as a dissolution inhibitor is obtained by reacting NAH-6, NAH-5, or NAH-4 with phenols in the presence of a dehydrohalogenation agent. For example, NAH-6 is reacted with an alcohol, a phenol, or a primary or secondary organic amine in the presence of a dehydrohalogenation agent.

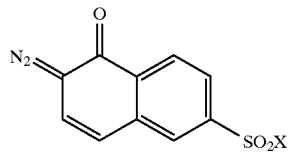

(II)

wherein X is chlorine or bromine.

Alcohols, phenols, and primary or secondary organic amines used in the above reaction include those compounds which are described in J. Kosai, "Light-Sensitive Systems", John Wily & Sons, Inc., New York, 1965, pp 339–357. In addition, usable phenols are those which are described in U.S. Pat. Nos. 3,046,120, 3,046,121, 3,061,430, 3,102,809, 3,106,465, 3,180,733, 3,184,310, 3,201,239, 3,635,705, OPI 58-150948/1983, OPI 58-17112/1983, OPI 58-182632/1983, OPI 59-165053/1984, OPI 60-134235/1985, OPI 60-146234/1985, OPI 60-163043/1985, OPI 61-97278/1986, OPI 61-209439/1986, OPI 62-10645/1987, OPI 62-10646/1987, OPI 62-36663/1987, OPI 63-24244/1988, OPI 63-110446/1988, OPI 63-119450/1988, OPI 63-178229/1988, OPI 63-180947/1988, OPI 63-208840/1988, OPI 63-279246/1988, OPI 63-305348/1988, OPI 64-17049/1989, OPI 1-147538/1989, OPI 1-177031/1989, OPI 1-189644/1989, OPI 1-291240/1989, OPI 1-291241/1989, OPI 1-291242/1989, OPI 1-291243/1989, OPI 2-2559/1990, OPI 2-2560/1990, OPI 2-309052/1990, OPI 2-32351/1990, OPI 2-32352/1990, OPI 2-40352/1990, OPI 2-40353/1990, OPI 2-59552/1990, OPI 284650/1990, OPI 2-110462/1990, and OPI 2-186351/1990. In particular, polyhydric phenols which are high in dissolution inhibition ability of alkali-soluble resins are preferable.

The reaction of NAH-6, NAH-5 or NAH-4 with alcohols, phenols, or primary or secondary organic amines is achieved using a conventional method known in the art. Specifically, one or more sulfonylhalides selected from NAH-6, NAH-5 and NAH-4 and a solvent such as acetone, methylethylketone, dioxane, tetrahydrofuran, acetonitrile, pyridine, methylcellosolve acetate, γ-butyrolactone, γ-valerolactone, dimethylimidazolidinone, N-methylpyrrolidone, acetonylacetone, or sulfolane are charged into a reaction vessel. Condensation is effected by dropping a basic catalyst into the vessel; for example, an inorganic basic catalyst such as sodium hydroxide, potassium hydroxide, sodium carbonate, potassium carbonate, or sodium hydrogen carbonate; or an organic basic catalyst such as diethylamine, diethanolamine, triethylamine, triethanolamine, N-n-butyldiethanolamine, tri-n-butylamine, pyridine, or picoline.

When the reaction is carried out using polyalcohols, polyhydroxyphenols, or polyamines, the reaction product is a mixture of compounds with different esterification or amidation numbers and with different esterification or amidation positions. The mixture can normally be used as such.

The positive photoresist composition according to the present invention is obtained by dissolving at least one of the photosensitive agents shown in (1) to (3) below and an alkali-soluble resin in an appropriate solvent, and filtering the resultant solution through a filter with a pore size of, for example, 0.2 μm:

(1) 6-alcohol ester, 6-phenol ester, or 6-sulfonamide, (2) a mixture of 6-phenol ester with 5-phenol ester and/or 4-phenol ester, (3) a condensation product of NAH-6 mixed with NAH-5 and/or NAH-4 and phenols.

The solvent used in the composition can be, for example, ethers such as dioxane, ethyleneglycol-dimethylether, ethyleneglycol-diethylether, propyleneglycol-dimethylether, and propyleneglycol-diethylether; monoethers such as ethyleneglycol-monomethylether, ethyleneglycol-monoethylether, propyleneglycol-monomethylether, and propyleneglycol-monoethylether; ketones such as methylethylketone, methylisobutylketone, cyclopentanone, and cyclohexanone; esters such as ethyl acetate, butyl acetate, methylcellosolve acetate, ethylcellosolve acetate, methoxypropyl acetate, ethoxypropyl acetate, dimethyl oxalate, methyl lactate, and ethyl lactate; amides such as N,N-dimethylformamide and N,N-dimethylacetamide; pyrrolidones such as N-methylpyrrolidone; lactones such as γ-butyrolactone; and sulfoxides such as dimethylsulfoxide. These solvents may be used alone or in combination. Concentration of the solution (total solid including additives) is appropriately 2% to 50% by weight.

The ratio of the alkali-soluble resin and the quinonediazide compound in the inventive positive photoresist composition is not specifically limited, but is typically 2 to 80 parts by weight, preferably 5 to 50 parts by weight, of the quinonediazide compound to 100 parts by weight of the alkali-soluble resin.

When the amount of the quinonediazide compound is less than 2 parts by weight, the resulting resist pattern is inferior in resolution, with increased film loss in the unexposed portion after development. When the amount exceeds 80 parts by weight, it is impossible to obtain a composition which has a high sensitivity.

The ratio of 6-phenol ester and 5-phenol ester and/or 4-phenol ester is not specifically limited, but is typically 5-ester and/or 4-ester in an amount of 1 to 10,000 parts by weight to 100 parts by weight of 6-ester. This ratio also applies to the case where phenols are reacted with NAH-6 and NAH-5 and/or NAH-4.

Furthermore, the inventive composition can additionally contain known polymer compounds in amounts of 50 parts by weight or less, preferably 20 parts by weight or less based on 100 parts by weight of the alkali-soluble resin. Such additives are used as needed to improve the developability, film strength, and/or storage stability of the composition. Such polymer compounds include natural polymer compounds such as rosin and shellac, and synthetic polymer compounds such as polyvinylformal, polyvinylbutyral, polyviylacetal, polyesters, epoxy resins, alkyd resins, polyurethane, polyamide, copolymer of styrene and maleic anhydride, acrylic ester polymers, copolymers of styrene with acrylic acid, methacrylic acid, or alkylesters thereof, and polyvinylpyrrolidone.

The positive photoresist composition according to the present invention can be mixed, as needed, with a print-out agent to form a visible image, halation prevention agents such as dyes or pigments, an adhesion auxiliary such as a silane coupling agent to improve adhesion of the substrate to the resist layer, and a surfactant to improve the applicability.

An example of the pattern formation method according to the present invention will now be described.

First, the inventive resin composition is coated on a substrate and dried to form a radiation-sensitive resin layer. Depending on the purpose, the substrate can be silicon, silicon dioxide, silicon nitride, polysilicon, ceramics, aluminum, copper, aluminum oxide, glass, ITO (indium tin oxide), plastic films, paper, or the like.

Coating can be achieved by conventional methods known in the art, e.g. rotary coating, wire bar coating, dip coating, air knife coating, roll coating, blade coating, curtain coating or the like. After the resin composition is coated on the substrate, the coated substrate is heat treated at about 200 to 150° C. The heat treatment is to reduce the concentration of solvent in the resin composition. It is preferably carried out at 50 to 150° C. for 10 seconds to 30 minutes. It is preferable to carry out the heat treatment until the solvent removal rate becomes relatively small, and the temperature and time are appropriately set according to the properties of the resin composition, solvent type, and coating thickness.

The coating film is then exposed to a specified pattern. The exposure light can be visible light, ultraviolet rays, X-rays, or an electron beam. Light sources for the exposure include fluorescent lamps, carbon arcs, xenon lamps, metal halide lamps, argon ion lasers, KrF excimer lasers, XeCl excimer lasers, and the like. Suitable X-ray sources include plasma and synchrotron radiations, and the electron beam sources can advantageously be thermoelectron and field radiations. Of these sources, it is particularly preferable to use the i-line of a mercury lamp or an argon ion laser.

The positive photoresist layer is then developed with an alkaline developing solution to form a pattern. The alkaline developing solution used in this step can be aqueous solutions of inorganic alkalis such as sodium hydroxide, potassium hydroxide, sodium carbonate, potassium carbonate, sodium silicate, sodium metasilicate, and ammonia water; primary amines such as ethylamine and n-propylamine; secondary amines such as diethylamine and di-n-propylamine; tertiary amines such as triethylamine and methyldiethylamine; alcohols such as dimethylethanolamine and triethanolamine; quaternary ammonium hydroxides such as tetramethylammonium-hydroxide, tetraethylammonium-hydroxide, and hydroxyethyl-trimethylammonium-hydroxide; alkylamines of cyclic amines such as pyrrole, piperidine, and morpholine; alcoholamines such as diethanolamine and triethanolamine; quaternary ammonium salts such as tetramethyammonium-hydroxide, tetraethylammonium-hydroxide, and trimethyl (2-hydroxyethyl)-ammonium-hydroxide; and cyclic amines such as pyrrole and piperidine.

The developing solution can be mixed, as needed, with other additives such as surfactants, wetting agents, and small amounts of organic solvents. After exposure and prior to development, the film may be subjected to post-exposure-bake (PEB) at 80 to 150° C. The PEB diffuses the photosensitive agent to reduce effects of a standing waves, thereby assisting in providing a good pattern.

DESCRIPTION OF THE PREFERRED EMBODIMENTS

Synthesis Example 1

Synthesis of Naphthoguinonediazide Compound A 4,4',4"-trihydroxy-triphenylmethane in an amount of 4.67 g (0.01 mole), 10.75 g (0.040 mole) of 1,2-naphthoquinone-(2)-diazide-6-sulfonylchloride, and 200 g of dioxane were charged in a 300-ml three-necked flask and stirred into solution. Into the solution, 4.45 g (0.040 mole) of triethylamine was dropped at 20 to 25° C. over a period of 30 minutes. After the completion of dropping, the mixture was reacted at 30° C. for 4 hours.

The reaction mixture was poured into 1 liter of ion exchanged water, the resulting precipitate was filtered and dried to obtain 13.29 g of 1,2-naphthoquinone-(2)-diazide-6-sulfonic ester of 4,4',4"-trihydroxy-triphenylmethane (naphthoquinonediazide compound A).

Synthesis Example 2

Synthesis of Naphthoguinonediazide Compound B 2,2-bis(2,4-dihydroxyphenyl)propane in an amount of 3.47 g (0.0133 mole), 10.75 g (0.040 mole) 1,2-naphthoquinone-(2)-diazide-6-sulfonylchloride, and 200 g of dioxane were charged in a 300-ml three-necked flask and stirred into solution. Into the solution, 4.45 g (0.040 mole) of triethylamine was dropped at 20 to 25° C. in 30 minutes. After the completion of dropping, the mixture was reacted at 30° C. for 4 hours.

The reaction mixture was poured into 1 liter of ion exchanged water, the resulting precipitate was filtered and dried to obtain 13.87 g of 1,2-naphthoquinone-(2)-diazide-6-sulfonic ester of 2,2-bis(dihydroxyphenyl)propane (naphthoquinonediazide compound B).

Synthesis Examples 3 and 4

Synthesis of Naphthoguinonediazide Compounds C and D (Comparative Example)

Synthesis was carried out using the same procedure as in Synthesis Examples 1 and 2, except that 1,2-naphthoquinone-(2)-diazide-5-sulfonylchloride was used in place of 1,2-naphthoquinone-(2)-diazide-6-sulfonylchloride, to obtain 1,2-naphthoquinone-(2)-diazide-5-sulfonic ester of 4,4',4"-trihydroxytriphenylmethane (naphthoquinonediazide compound C) and 1,2-naphthoquinone-(2)-diazide-5-sulfonic ester of 2,2-bis(2,4-dihydroxyphenyl)propane (naphthoquinonediazide compound D).

Synthesis Example 5

Synthesis of Novolac Resin m-cresol in an amount of 60 g, 40 g of p-cresol, 55 g of 37% by weight formaldehyde aqueous solution, and 0.05 g of oxalic acid were charged in a 300-ml three-necked flask and reacted with stirring in a 100° C. oil bath for 5 hours. After the completion of reaction, the reaction mixture was cooled and then evacuated. The temperature of the mixture was gradually increased to 150° C. to remove water and monomers. The resulting novolac resin had a polystyrene-equivalent weight-average molecular weight of 8,200.

Examples 1-2 and Comparative Examples 1–4

The photosensitive agents and alkali-soluble resin shown in Table 1 were dissolved in ethylcellosolve acetate to a solid content of 30% by weight, and filtered through a 0.2 µm membrane filter to obtain the photoresist compositions. These photoresist compositions were coated on a quartz plate, dried at 80° C. for 30 minutes, exposed to i-line radiation, and measured for parameters A and B which are used in Dill's proposal.

Each photoresist composition was individually coated on a silicon wafer to a film thickness of approximately 1.2 µm, and dried at 80° C. for 30 minutes. After exposure using i-line radiation, the films were developed by dipping in a 2.38% aqueous solution of tetramethylammonium-hydroxide (Tokyo Oka Kogyo, NMD-3) at 25° C. for 60 seconds, and then measured for film residual rate, relative sensitivity, and γ value.

The tests results are shown in Table 2.

TABLE 1

| Photoresist composition | | Photosensitive agent | Alkali-soluble resin | A*1 ($\mu m^{-1}$) | B*1 ($\mu m^{-1}$) |
|---|---|---|---|---|---|
| Example 1 | (1) | A 30 wt. parts | Novolac resin | 0.33 | 0.06 |
| | (2) | A 25 wt. parts | 100 wt parts | 0.30 | 0.06 |
| | (3) | A 15 wt. parts | | 0.19 | 0.06 |
| Comparative Example 2 | (1) | C 30 wt. parts | Novolac resin | 0.86 | 0.06 |
| | (2) | C 25 wt. parts | 100 wt parts | 0.78 | 0.06 |
| | (3) | C 15 wt. parts | | 0.49 | 0.06 |
| Example 2 | (1) | B 30 wt. parts | 100 wt parts | 0.31 | 0.07 |
| | (2) | B 15 wt. parts | | 0.17 | 0.06 |
| Example 3 | (1) | D 30 wt. parts | 100 wt parts | 1.04 | 0.06 |
| | (2) | D 15 wt. parts | | 0.62 | 0.06 |
| Comparative Example 3*2 | | Nagase Denshi Kogyo | NRA18E x 2 | 0.64 | 0.09 |
| Comparative Example 4*2 | | Fuji Hunt FHi-300 | | 0.65 | 0.02 |

*1Parameters in the exposure process model proposed by Dill.
*2Values described in Nikkei Microdevice (Nippon Keizai Shinbunsha) November 1989, p178.

TABLE 2

| | | film residual rate | Relative sensitivity*3 | γ-value |
|---|---|---|---|---|
| Example 1 | (1) | 99% | 2.3 | 2.4 |
| | (2) | 99% | 2.0 | 2.2 |
| | (3) | 98% | 1.0 | 2.0 |
| Comparative Example 1 | (1) | 94% | 1.0 | 1.8 |
| | (2) | 93% | 0.7 | 1.4 |
| | (3) | 91% | 0.5 | 1.1 |
| Example 2 | (1) | 99% | 2.2 | 2.7 |
| | (2) | 99% | 0.8 | 1.7 |
| Comparative Example 2 | (1) | 97% | 1.0 | 1.5 |
| | (2) | 94% | 0.2 | 1.0 |

*3Relative value of exposure time to complete removal of exposed portion

As can be seen from Table 1, the photoresist layers of the Examples are small in both value A, indicating the ratio of transmissivity before and after exposure, and value B, indicating transparency after exposure: they exhibit high transparency both before and after exposure.

From Table 2, the photosensitive agents in the photoresists of the Examples are very high in dissolution inhibition ability, compared to those in Reference Examples. Therefore, the photoresist according to the present invention achieves high film residual rate and high γ value using a small amount of the photosensitive agent.

Example 3 and Comparative Example 5

The photoresist composition of Example 1-(1) was coated with a spinner on a silicon wafer to film thickness of 1.2 μm, and dried in an oven at 80° C. for 30 minutes.

As a comparative example, positive photoresist OFPR-800 of Tokyo Oka Kogyo was coated using the same procedure to form a resist film on a silicon wafer.

These films were irradiated with 488-nm light from an argon ion laser, developed by dipping in a 2.38% tetramethylammonium hydroxide aqueous solution (Tokyo Oka Kogyo NMD-3) at 25° C. for 60 seconds, and then measured for the percentage of the initial resist thickness remaining after development (hereinafter referred to as "film residual rate" and relative sensitivity.

The test results are shown in Table 3.

TABLE 3

| | Film residual rate | Relative sensitivity |
|---|---|---|
| Example 3 | 99% | 0.4 |
| Comparative Example 5 | 87% | 1.0 |

It can be seen from Table 3 that the photoresist composition of this Example is highly sensitive to argon ion laser and high in residual rate.

Example 4

The photoresist composition of Example 1-(3) was coated with a spinner on a silicon wafer to a film thickness of 1.1 μm, and dried on a hot plate at 110° C. for 90 seconds. The film was exposed through a test chart mask using an i-line radiation reduced projection exposure device: NSR 1505 i 6A Wafer Stepper (Nicon, NA=0.45), and developed with a 38% tetramethylammonium hydroxide aqueous solution (Tokyo Oka Kogyo NMD-3) at 25° C. for 60 seconds.

Electron microscopic observation of the resulting pattern revealed that a 0.4 μm l/s (line(s) and space(s)) pattern was formed in a rectangular shape without film loss.

Synthesis Example 6
Synthesis of Naphthoquinonediazide Compound E

This synthesis was carried out using the same procedure as in Synthesis Example 1, except that 3.42 g (0.015 mole) of 2,4,4'-trihydroxydiphenylmethane was used in place of 4,4',4"-trihydroxytriphenylmethanee, to obtain 1,2-naphthoquinone-(2)-diazide-6-sulfonic ester of 2,4,4'-trihydroxydiphenylmethane (naphthoquinonediazide compound E).

Synthesis Example 7
Synthesis of Naphthoquinonediazide Compound F

The synthesis was carried out using the same procedure as in Synthesis Example 2, except that 3.09 g (0.0133 mole) of 2,3,4,4'-tetrahydroxydiphenylmethane was used in place of 2,2-bis(2,4-dihydroxyphenyl)propane, to obtain 1,2-naphthoquinone-(2)-diazide-6-sulfonic ester of 2,3,4,4'-tetrahydroxydiphenylmethane (naphthoquinonediazide compound F).

Synthesis Example 8
Synthesis of Naphthoquinonediazide Compound G

Using the same procedure as in Synthesis Example 1, 3.09 g (0.0133 mole) of 2,3,4,4'-tetrahydroxydiphenyl-methane, 5.0 g (0.0185 mole) of 1,2-naphthoquinone-(2)-diazide-6-sulfonylchloride, and 7.5 g (0.027 mole) of 1,2-naphthoquinone-(2)-diazide-5-sulfonylchloride were used to obtain a mixed ester of 1,2-naphthoquinone-(2)-diazide-6-sulfonic acid and 5-sulfonic acid of 2,3,4,4'-tetrahydroxy-diphenylmethane (naphthoquinonediazide compound G).

Synthesis Examples 9 and 10
Synthesis of Naphthoquinonediazide Compounds H and I Synthesis was carried out using the same procedure as in Synthesis Examples 2 and 7, except that 1,2-naphthoquinone-(2)-diazide-5-sulfonylchloride was used in place of 1,2-naphthoquinone-(2)-diazide-6-sulfonylchloride, to obtain 1,2-naphthoquinone-(2)-diazide-5-sulfonic ester of 2,2-bis(2,4-dihydroxyphenyl)propane (naphthoquinonediazide compound H) and 1,2-naphthoquinone-(2)-diazide-5-sulfonic ester of 2,3,4,4'-tetrahydroxy-diphenylmethane (naphthoquinonediazide compound I).

Synthesis Examples 11 and 12
Synthesis of naphthoquinonediazide Compounds J and K The synthesis was carried out using the same procedure as in Synthesis Example 2, except that 3.27 g (0.0133 mole) of 2,3,4,4'-tetrahydroxy-benzophenone was used in place of 3.47 g of 2,2-bis(2,4-dihydroxyphenyl)propane, 1,2-naphthoquinone-(2)-diazide-5-sulfonylchloride and 1,2-naphthoquinone-(2)-diazide-4-sulfonylchloride in place of 1,2-naphthoquinone-(2)-diazide-6-sulfonylchloride, to obtain 1,2-naphthoquinone-(2)-diazide-5-sulfonic ester (quinone-diazide compound J) and 1,2-naphthoquinone-(2)-diazide-4-sulfonic ester (naphthoquinonediazide compound K) of 2,3,4,4'-tetrahydroxybenzophenone.

Examples and Comparative Examples

Examples 6 to 11 and Comparative Examples 6 to 8 were carried out using compounds E to K obtained in the Synthesis Examples. The quinonediazide compounds of the compositions shown in Table 4 and the novolac resin obtained in Synthesis Example 5 were dissolved in ethylcellosolve acetate to a solid content of 30% by weight, and filtered by a 0.2 μm membrane filter to prepare photoresist compositions I to IX.

These photoresist compositions were coated on a quartz plate, dried at 80° C. for 30 minutes, exposed using g-line or i-line radiation, and measured for parameters A and B of the photoreaction model proposed by Dill.

In addition, the photoresist compositions were coated on a quartz plate to a film thickness of approximately 1.2 μm, and dried at 80° C. for 30 minutes. After exposure to g-line or i-line radiation, the films were developed by dipping in a 2.38% tetramethylammonium hydroxide aqueous solution (Tokyo Oka Kogyo, NMD-3) at 25° C. for 60 seconds, and measured for film residual rate and γ-value.

The test results are shown in Table 4.

Example 12

The positive photoresist composition I of Example 6 was coated with a spinner on a silicon wafer to a film thickness of 1.1 μm, and dried on a hot plate at 110° C. for 90 seconds. The film was exposed through a test chart mask using an i-line radiation reduced projection exposure device: NSR 1505 i 6A Wafer Stepper (Nicon, NA=0.45), and developed with a 38% tetramethylammonium hydroxide aqueous solution (Tokyo Oka Kogyo NMD-3) at 25° C. for 60 seconds to form a pattern.

Electron microscopic observation of the resulting pattern revealed that a 0.4 μm 1/s pattern was formed in a rectangular shape without film loss.

As described above with reference to the Examples, the present invention can provide a positive photoresist composition which has a high transparency to i-line radiation, and a large difference in solubility in the developing solution between exposed and unexposed portions, and a pattern formation method which can form a good pattern using the composition. Therefore, the positive photoresist composition and the pattern formation method according to the present invention are suitable for use in the formation of fine patterns, for example, for use in various semiconductor ICs and magnetic valves.

Furthermore, the present invention can provide a positive photoresist composition which is highly sensitive to light emitted by an argon laser, exhibits a high film residual rate, is useful in pattern formation method, and is especially suitable for the fabrication, for example, of disk base plates.

In addition, with the present invention, since parameter A can be flexibly set while parameter B is kept constant, parameter A can be adequately set to provide a high film residual rate and high γ value.

Therefore, the positive photoresist composition according to the present invention is suitable for use, for example, in the formation of fine patterns of various semiconductor IC's and magnetic valves.

We claim:

1. A positive photoresist composition comprising a mixture of an alkali-soluble resin and an effective amount of a photosensitive agent comprising a phenol ester of 1,2-

TABLE 4

| | Photoresist composition | Quinone diazide compound (wt. %) | Exposure | Parameters A | B | Film residual rate | γ value |
|---|---|---|---|---|---|---|---|
| Example 6 | I | A (15) I (10) | i-line | 0.53 | 0.06 | 99% | 2.1 |
| Example 7 | II | B (10) H (15) | g-line | 0.95 | 0.05 | 98% | 1.7 |
| Example 8 | III | G (25) | i-line | 0.57 | 0.06 | 99% | 1.8 |
| Example 9 | IV | E (20) I (5) | g-line | 0.90 | 0.05 | 99% | 2.0 |
| Example 10 | V | F (5) J (25) | g-line | 1.05 | 0.06 | 99% | 2.1 |
| Example 11 | VI | F (20) K (10) | i-line | 0.45 | 0.07 | 99% | 2.2 |
| Comparative Example 6 | VII | H (25) | i-line | 0.89 | 0.06 | 96% | 1.4 |
| Comparative Example 7 | VIII | J (30) | g-line | 1.00 | 0.06 | 98% | 1.8 |
| Comparative Example 8 | IX | A (25) | i-line | 0.30 | 0.06 | 99% | 2.4 | naphthoquinone-(2)-diazide-6-sulfonic acid, said resin and photosensitive agent being present in a ratio of 100:2-80.

2. The composition of claim 1 wherein said photosensitive agent comprises
   (a) a phenol ester of 1,2-naphthoquinone-(2)-diazide-6-sulfonic acid, and
   (b) at least one of a phenol ester of 1,2-naphthoquinone-(2)-diazide-5-sulfonic acid, and a phenol ester of 1,2-naphthoquinone-(2)-diazide-4-sulfonic acid.

3. The composition of claim 1 wherein said photosensitive agent comprises
   (a) a condensation product of a phenol and 1,2-naphthoquinone-(2)-diazide-6-sulfonylhalide, and
   (b) at least one of a condensation product of a phenol and 1,2-naphthoquinone-(2)-diazide-5-sulfonylhalide, and a condensation product of a phenol and 1,2-naphthoquinone-(2)-diazide-4-sulfonylhalide.

4. A method of pattern formation comprising:
   (1) forming a positive photoresist layer on a substrate using the positive photoresist composition of claim 1,
   (2) exposing the positive photoresist layer according to a predetermined pattern, and
   (3) developing the positive photoresist layer with an alkaline developing solution.

5. The method of claim 4 wherein the positive photoresist layer is exposed to i-line radiation from a mercury lamp.

6. The method of claim 4 wherein the positive photoresist layer is exposed to an argon ion laser light.

7. A method of pattern formation comprising:
   (1) forming a positive photoresist layer on a substrate using the positive photoresist composition of claim 2,
   (2) exposing the positive photoresist layer according to a predetermined pattern, and
   (3) developing the positive photoresist layer with an alkaline developing solution.

8. The method of claim 7 wherein the positive photoresist layer is exposed to i-line radiation from a mercury lamp.

9. The method of claim 7 wherein the positive photoresist layer is exposed to an argon ion laser light.

10. A method of pattern formation comprising:
    (1) forming a positive photoresist layer on a substrate using the positive photoresist composition of claim 3,
    (2) exposing the positive photoresist layer according to a predetermined pattern, and
    (3) developing the positive photoresist layer with an alkaline developing solution.

11. The method of claim 10 wherein the positive photoresist layer is exposed to i-line radiation from a mercury lamp.

12. The method of claim 10 wherein the positive photoresist layer is exposed to an argon ion laser light.

* * * * *